(12) United States Patent
Pathak et al.

(10) Patent No.: US 7,645,474 B1
(45) Date of Patent: Jan. 12, 2010

(54) METHOD AND SYSTEM OF PURIFYING POLYMERS FOR USE WITH IMPLANTABLE MEDICAL DEVICES

(75) Inventors: Jaya Pathak, Carlsbad, CA (US); Fuh-Wei Tang, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 486 days.

(21) Appl. No.: 10/631,228

(22) Filed: Jul. 31, 2003

(51) Int. Cl.
*A61L 33/00* (2006.01)
(52) U.S. Cl. ........................... 427/2.1; 427/592
(58) Field of Classification Search .................. 427/2.1, 427/592
See application file for complete search history.

(56) References Cited

U.S. PATENT DOCUMENTS

| | | | |
|---|---|---|---|
| 4,117,714 A * | 10/1978 | Goodson et al. | 73/31.03 |
| 4,329,383 A | 5/1982 | Joh | 428/36 |
| 4,384,072 A | 5/1983 | Newman et al. | 525/356 |
| 4,526,579 A * | 7/1985 | Ainpour | 604/265 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,941,870 A | 7/1990 | Okada et al. | 600/36 |
| 4,977,901 A | 12/1990 | Ofstead | 128/772 |
| 4,990,222 A | 2/1991 | Aigner et al. | 203/91 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,415,473 A | 5/1995 | Nakano et al. | 366/83 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,569,463 A | 10/1996 | Helmus et al. | 424/426 |

(Continued)

FOREIGN PATENT DOCUMENTS

EP      0 301 856      2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Timothy H Meeks
*Assistant Examiner*—Jimmy Lin
(74) *Attorney, Agent, or Firm*—Squire, Sanders & Dempsey L.L.P.

(57) ABSTRACT

A method and system for purifying polymers to use with medical devices, particularly for a drug eluting stent, is described.

25 Claims, 2 Drawing Sheets

U.S. PATENT DOCUMENTS

| | | | |
|---|---|---|---|
| 5,578,073 A | 11/1996 | Haimovich et al. | 623/1 |
| 5,597,235 A | 1/1997 | Barnes et al. | 366/76.6 |
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,756,553 A * | 5/1998 | Iguchi et al. | 514/772.3 |
| 5,756,659 A * | 5/1998 | Hughes et al. | 528/501 |
| 5,762,944 A * | 6/1998 | Inoue et al. | 424/400 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,096,369 A * | 8/2000 | Anders et al. | 427/2.3 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,156,345 A * | 12/2000 | Chudzik et al. | 424/484 |
| 6,165,212 A | 12/2000 | Dereume et al. | 623/1.13 |
| 6,203,551 B1 | 3/2001 | Wu | 606/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 2001/0000230 A1 * | 4/2001 | Bernstein et al. | 424/486 |
| 2001/0009656 A1 * | 7/2001 | Greff et al. | 424/1.25 |
| 2001/0018469 A1 | 8/2001 | Chen et al. | 523/121 |
| 2001/0037145 A1 | 11/2001 | Guruwaiya et al. | 623/1.15 |
| 2002/0031616 A1 * | 3/2002 | Neoh et al. | 427/553 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2004/0063663 A1 * | 4/2004 | Buchanan et al. | 514/58 |
| 2005/0106203 A1 * | 5/2005 | Roorda et al. | 424/423 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |

| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272:278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

U.S. Appl. No. 10/198,912, filed Jul. 19, 2002 (36 pp.).

* cited by examiner

METHOD AND SYSTEM OF PURIFYING POLYMERS FOR USE WITH IMPLANTABLE MEDICAL DEVICES

BACKGROUND OF THE INVENTION

1. Field of the Invention

This invention is directed to methods and systems for purifying polymers used for medical devices, such as drug eluting stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A blend which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

A potential shortcoming of the foregoing method of medicating stents is that the commercially available polymers can contain impurities that trigger adverse biological responses to the stent when implanted into a biological lumen. The polymers can contain impurities such as catalysts, initiators, processing aids suspension aids, unreacted monomers and oligomers or other low molecular weight species, even though the polymer is sold as a "food packaging grade" polymer by the manufacturer. Some of the processes that are employed to purify polymers used in stent coatings can be time consuming, costly and can produce toxic effluents that are environmentally harmful. Thus, there is a need for processes of purifying polymers that does not suffer from the aforementioned drawbacks. The present invention provides a method and system to meet this need.

SUMMARY

In accordance with one aspect of the invention, a method of manufacturing an implantable medical device is disclosed, including purifying a polymer by introducing a polymer into a mixing apparatus; introducing a fluid into the mixing apparatus; mixing the fluid with the polymer; removing at least a volume of the fluid from the mixing apparatus such that an impurity is completely or at least partially removed with the fluid; and collecting the polymer after removal of the impurity; and then coating an implantable medical device with the purified polymer, or fabricating the implantable medical device with the purified polymer. In one embodiment, the method further includes exposing the fluid to a temperature equal to or greater than the boiling temperature of the fluid at ambient pressure prior to removing the fluid from the mixing apparatus. In another embodiment, the polymer is exposed to a temperature equal to or greater than the melting temperature of the polymer. In a further embodiment, the fluid is of a type to physically entrap the impurity without dissolving the impurity. In yet another embodiment, the fluid is of a type to dissolve the impurity.

In another aspect of the invention, a method of manufacturing a coating for an implantable medical device is disclosed, comprising purifying a thermoplastic polymer, the purifying including introducing a thermoplastic polymer having an impurity into an extruder, introducing a fluid into the extruder, mixing the fluid with the polymer, removing at least a portion of the fluid and impurity from the extruder, and collecting the polymer after removal of the impurity; and applying a composition to an implantable medical device, the composition including the purified polymer, a solvent and optionally a therapeutic agent. In one embodiment, the polymer is selected from the group consisting of an ethylene vinyl alcohol copolymer, poly(butyl methacrylate), poly(vinylidene fluoride-co-hexafluororpropene), polyvinylidene fluoride, poly(L-lactic acid), poly(caprolactone), an ethylene-vinyl acetate copolymer and polyethylene glycol. In another embodiment, the fluid is selected from the group consisting of water, isopropyl alcohol, methanol, FLUX REMOVER AMS, acetone, ethanol, dimethyl acetamide, acetonitrile, dimethyl formamide, cyclohexane, dimethyl sulfoxide, and combinations thereof.

In a further aspect, a system for removing an impurity from a polymer is disclosed, including an extruder, the extruder having a first orifice configured to receive a polymer; an element configured to convey the polymer through the extruder, an injection port configured to receive a fluid, an extraction port configured to remove the fluid; and a second orifice configured to eject a polymer; a pump for introducing the fluid into the injection port; and a vacuum in communication with the extraction port. In one embodiment, the extruder further comprises a zone capable of heating the polymer. In another embodiment, the extraction port is positioned in close proximity to the injection port.

DETAILED DESCRIPTION

Methods of Purification

Before a polymer is used for an implantable medical device, the polymer should be purified. The present invention provides a method of purifying a polymer (e.g., thermoplastic polymer) for use with an implantable medical device. The method includes introducing a polymer having an impurity into a mixing apparatus. The method can include reducing the viscosity of the polymer to produce a workable range of viscosity, for example, so that the polymer is in a liquid form or state. Next, a fluid is introduced into the mixing apparatus and mixed with the liquid form of the polymer. As the fluid is mixed with the polymer, the fluid acts to strip or remove impurities from the polymer. After the impurities have been removed from the polymer by the fluid, the fluid containing the impurity is removed from the mixing apparatus and the purified polymer is collected. By using the methods of the present invention, polymers can be purified to remove a significant amount of low molecular weight species such as residual catalysts, initiators, processing aids, suspension aids, unreacted monomers and oligomers.

Representative examples of polymers that can be purified by using the methods of the present invention include poly (hydroxyvalerate), poly(lactide-co-glycolide), poly(hydroxybutyrate), poly(hydroxybutyrate-co-valerate), polyorthoester, polyanhydride, poly(glycolic acid), poly(D,L-lactic acid), poly(glycolic acid-co-trimethylene carbonate), poly(trimethylene, carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of polymers that can be especially well suited for purification by using a method of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), poly(L-lactic acid), poly(caprolactone), ethylene-vinyl acetate copolymers, polyethylene glycol.

A polymer having an impurity can be introduced into a mixing apparatus in a solid form (e.g., such as pellets or a fine powder) or a melted form (e.g., as a polymer pre-heated to a temperature at or above the melting temperature of the polymer). As the polymer is introduced into the mixing device, or any time during the purification process, a gas can be delivered to the mixing device to reduce the amount of degradation or discoloration experienced by the polymer. The gas can reduce the amount of degradation or discoloration by removing degradation agents. For example, the gas can remove atmospheric oxygen from the mixing apparatus. Atmospheric oxygen, if not removed from the mixing apparatus, can cause discoloration during the purification process. Representative examples of gases that can be delivered include inert gases such as nitrogen, argon, etc.

As the polymer is mixed in the mixing apparatus, the polymer should be in a substantially liquid form. The viscosity of the polymer in the mixing apparatus can be at the maximum, about 10,000 poises at 1 atm to about 20,000 poises at 1 atm. If the polymer is too viscous (e.g., has been introduced into the mixing apparatus as a solid form), the polymer should be exposed to mixing conditions that decrease the viscosity. For example, the mixing parameters (e.g., shear rate) can be selected so that the polymer's viscosity is decreased. Also, the polymer can be exposed to a sufficient temperature that decreases the viscosity of the polymer. For instance, the polymer can be heated by elements integrated with the mixing apparatus to a temperature equal to or greater than the temperature at which the polymer exhibits characteristics of a liquid such as the ability to flow. In one embodiment, the polymer is exposed to a temperature equal to or greater than the melting temperature of the polymer. The melting temperature of a crystalline or semi-crystalline polymer is the temperature at which the last trace of crystallinity in the polymer disappears as a sample is exposed to increasing heat. The melting temperature of a polymer is also know as the fusion temperature. Methods of measuring melting temperatures are understood by one of ordinary skill in the art and are discussed by, for example, L. H. Sperling, Introduction to Physical Polymer Science, Wiley-Interscience; New York, (3rd ed. 2001), and R. F. Boyer, in Encyclopedia of Polymer Science and Technology, Suppl. Vol. 2, N. M. Bikales, ed., Interscience, New York (1977).

In the next step of the process, a fluid is introduced into the mixing apparatus. The fluid acts to strip or remove the impurity from the polymer. The fluid can be introduced into the mixing apparatus in either a liquid or gas/vapor form. Additionally, more than one fluid can be introduced into the mixing apparatus. Representative injection rates of the fluid can be from about 100 ml/hr to about 1200 ml/hr, and more narrowly 490 ml/hr to 1000 ml/hr.

The fluid can be selected in order to remove the known or suspected impurity in the polymer. For example, impurities such as sodium acetate, and lower molecular weight monomers and oligomers can be removed from an ethylene vinyl alcohol copolymer. Without being bound by any particular theory, it is believed that the fluid can remove an impurity because the fluid can dissolve the impurity and thus remove the impurity from the polymer mass. On the other hand, it is also believed that some fluids are capable of removing an impurity by physically entrapping the impurity without dissolving the impurity or only partially dissolving the impurity. In other words, it is believed that the fluid can physically force the impurity out of the polymer and to the surface of the polymer mass, where the impurity can be extracted from the mixing apparatus.

In one embodiment of the present invention, two different fluids are used to extract an impurity. A first fluid is capable of acting as a solvent for the impurity. For example, inorganic salts such as state salt and sodium acetate can be removed from poly(butyl methacrylate) by being dissolved in water.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the impurity in 1 ml of the solvent, and more narrowly 0.5 mg in 1 ml at ambient temperature and ambient pressure. A second fluid can act as a non-solvent for the impurity. For example, low molecular weight components (i.e., molecules having less than 1000 daltons) can be removed by being suspended by water. "Non-solvent" is defined as a substance incapable of dissolving the other substance. The non-solvent should be capable of dissolving only less than 0.1 mg of the impurity in 1 ml of the non-solvent at ambient temperature and ambient pressure, and more narrowly only less than 0.05 mg in 1 ml at ambient temperature and ambient pressure.

Representative examples of fluids that can remove an impurity include nitrogen, argon, air, water, isopropyl alcohol, methanol, FLUX REMOVER AMS, acetone, ethanol, dimethyl acetamide (DMAC), acetonitrile, dimethyl formamide (DMF), cyclohexane, dimethyl sulfoxide (DMSO), and mixtures thereof; FLUX REMOVER AMS is a trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance methanol, with trace amounts of nitromethane.

After the fluid has removed the impurity from the polymer mass, if the fluid is in a liquid form, then the fluid is heated to a temperature equal to or greater than the boiling point of the fluid at ambient pressure. The fluid in the vapor form containing the impurity is removed from the mixing apparatus. The fluid containing the impurity can be allowed to evaporate from the mixing apparatus under 1 atm, or the fluid can be extracted under a vacuum or reduced pressure, for example a pressure less than less than about 300 mm Hg, or more narrowly, less than about 10 mm Hg.

The following Table 1 provides selected properties for representative examples of fluids:

TABLE 1

| FLUID | VAPOR PRESSURE (mm Hg) @ 20° C. | BOILING POINT (° C.) @ 1 atm |
| --- | --- | --- |
| Water | 17.5 | 100 |
| Isopropyl alcohol | 32.4 | 82 |
| Methanol | 97 | 65 |
| DMAC | 1.3 | 166 |
| Acetone | 185 | 56 |
| Ethanol | 40 | 78 |
| DMSO | 0.6 | 189 |
| DMF | 2.7 | 153 |
| Cyclohexane | 77.5 | 49 |

After the impurity has been removed from the polymer, the purified polymer can be collected from the mixing apparatus. For example, the purified polymer can be pressurized and discharged from the mixing apparatus through a die. Additionally, the purified polymer can be extracted into a cooling bath or a stainless steel conveyer belt in preparation for post-processing.

System for Polymer Purification

Figure 1:
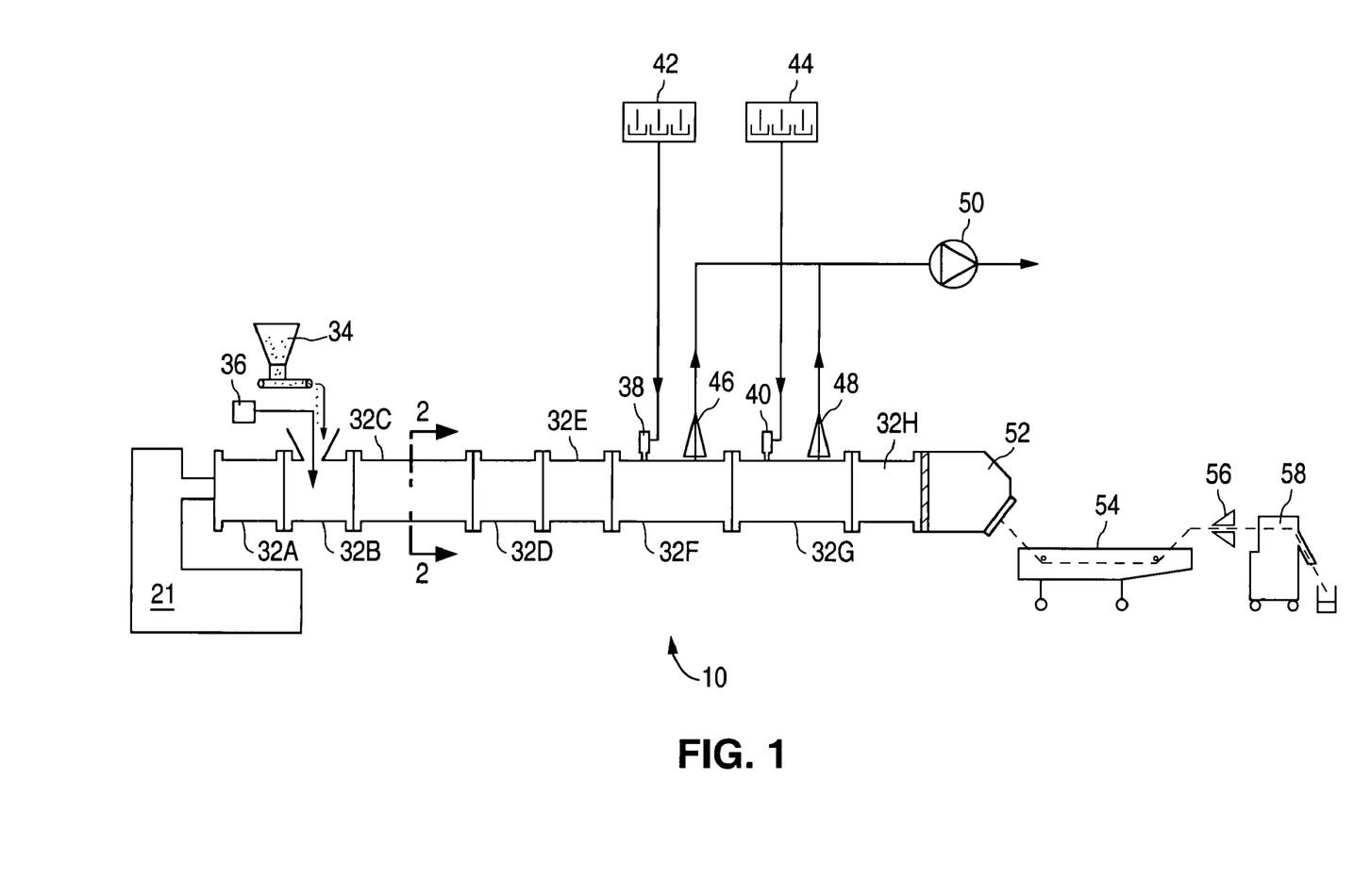
FIG. 1 is an illustration of a system including a twin screw extruder for purifying a polymer in accordance with an embodiment of the present invention.

Representative examples of mixing apparatuses for the present invention include single screw extruders, intermeshing co-rotating and counter-rotating twin-screw extruders and other multiple screw masticating extruders. FIG. 1 illustrates an example of a twin screw extruder 10. The configuration illustrated in FIG. 1 is an intermeshing co-rotating twin screw extruder. However, other configurations for a twin screw extruder are contemplated as useful with the process of the present, invention, including multiple extruders arranged in a cascaded fashion with the material passing continuously from one extruder to the next.

Figure 2:
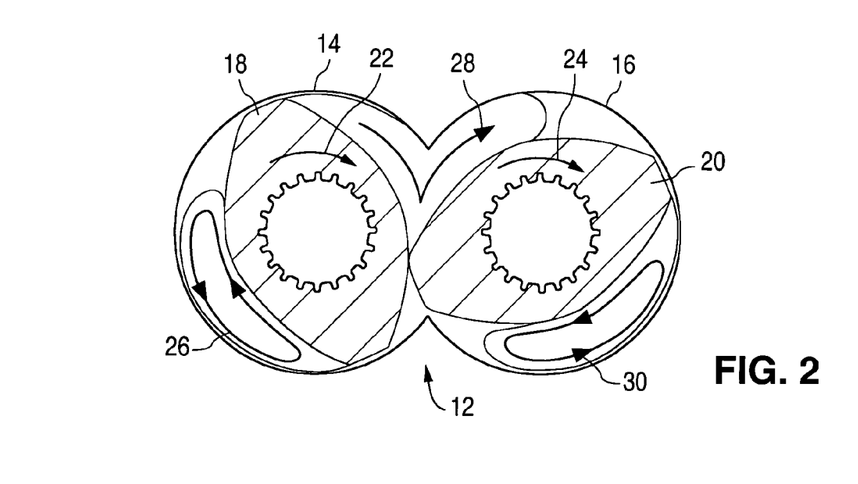
FIG. 2 is a cross-section of the twin screw extruder along the line 2-2 in FIG. 1.

Twin screw extruder 10 can include a longitudinal chamber 12. Referring to FIG. 2, chamber 12 has a pair of central cylinders 14 and 16 which house a pair of corresponding co-rotating twin extrusion screws 18 and 20, respectively. Each screw 18 and 20 can be mounted on a shaft that is integrated with a gear box housed by a motor 21. As indicated by arrows 22 and 24, each screw 18 and 20 can be configured to rotate within chamber 12 to convey the polymer in chamber 12. Arrows 26, 28 and 30 show the polymer flow within chamber 12 as the polymer is conveyed along twin screw extruder 10.

The configuration of the twin screws can be any suitable configuration that allows the twin screws to mix the material introduced into twin screw extruder 10, and convey the material through extruder 10. In one embodiment, the configuration illustrated in FIG. 3, as further described in Example 1, is used.

Twin screw extruder 10 can have a multiple number of barrels which act as discrete mixing zones. The barrels can have a total length to diameter ratio in the range of about 32-52, and more narrowly, about 36-44. In each of these mixing zones or barrels, the shear rate, shear stress, energy flux plastics material flow and temperature can be individually controlled. By controlling these particular process variables in each zone, the process of the present invention can effectively remove impurities from the polymer. Twin screw extruder 10 can have any suitable number of barrels for mixing the polymer. For example, twin screw extruder 10 can have one to fifteen barrels, more narrowly from eight to thirteen barrels. As illustrated in FIG. 1, twin screw extruder 10 has eight barrels marked 32A through 32H, including one "dummy barrel" (barrel 32A), and two double length barrels (barrels 32F and 32G). Each of the barrels can have a separate temperature control that can heat or cool the contents as needed.

The polymer can be introduced into twin screw extruder 10 by a feeder 34 into second barrel 32B. As noted above, first barrel 32A can act as a "dummy barrel." Representative examples of feeder 34 include a twin screw gravimetric feeder or a belt resin feeder. To realize greater process efficiency, the polymer can be introduced into the process by means of individually metered, continuous mass flow streams through feeder 34.

Twin screw extruder 10 can be in communication with a gas source 36. Gas source 36 can be used to deliver or introduce a gas that is capable of reducing the amount of degradation experienced by the polymer during the purification process. By way of example, gas source 36 can be in communication with second barrel 32B.

Figure 3:
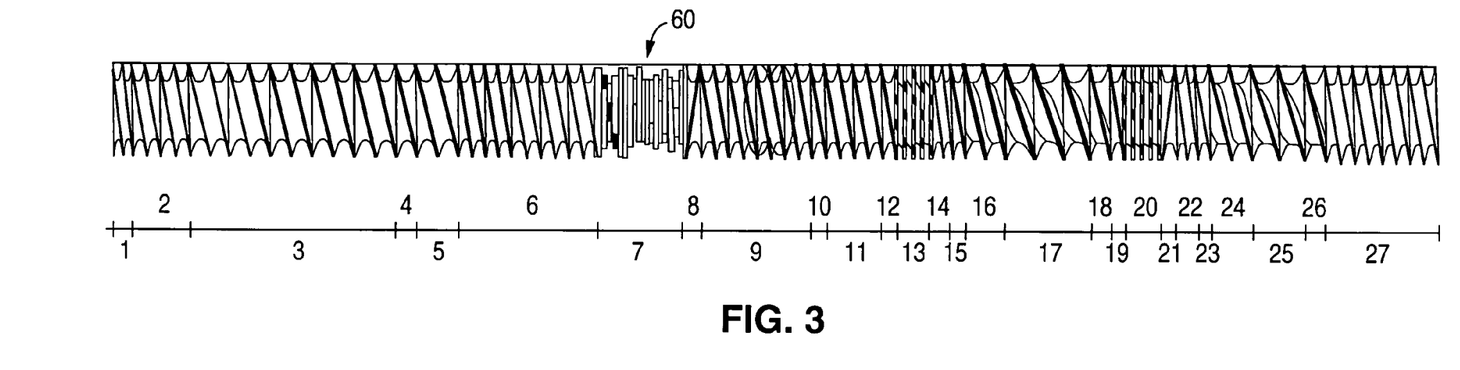
FIG. 3 is a side view of a twin screw configuration as referred to in the Example.

Once the polymer is introduced into twin screw extruder 10, the polymer is conveyed from one end to the other by twin screws 18 and 20. As the polymer is conveyed, the polymer should be in a liquid form. The polymer can be exposed to a temperature that decreases the viscosity of the polymer. The polymer can be heated at any point along the length of twin screw extruder 10, for example, at second and third barrels 32B and 32C. Furthermore, the viscosity of the polymer can be decreased by mechanical means, such as by kneading blocks that are housed in one or more barrels such as kneading block 60, as illustrated in FIG. 3.

The fluid that is capable of stripping or removing the impurity from the polymer can be introduced into twin screw extruder 10 at any point along chamber 12. Referring to FIG. 1, by way of example, the fluid can be introduced into twin screw extruder 10 through a first injection port 38 integrated with sixth barrel 32F and a second injection port 40 integrated with seventh barrel 32G of twin screw extruder 10. Different fluids, or the same fluids at different rates, can be directed into first injection port 38 and second injection port 40, respectively.

Twin screw extruder 10 can be constructed so that the pressure in chamber 12 is sufficiently low at the point where the fluid in injected so that the fluid can be injected into chamber 12 without being ejected or blown-out from chamber 12. For instance, the screw configuration of twin screw extruder 10 can be arranged so that there is a rotational orientation along sixth and seventh barrels 32F and 32G that reduces the pressure in chamber 12 at these points to about atmospheric pressure.

In one embodiment, a first fluid pump 42 is in communication with first injection port 38, and a second fluid pump 44 is in communication with second injection port 40. First and second fluid pumps 42 and 44 can be configured to provide measured pressure to meet a selected injection rate. A representative example of a pump that can be used for first and second pumps 42 and 44 is a piston pump available from American LEWA, Inc., Holliston, Mass.

After the fluid has captured the impurity and is in a vapor form, the fluid containing the impurity can be removed from twin screw extruder 10. Twin screw extruder 10 can have a first extraction port 46 and a second extraction port 48. Extraction ports 46 and 48 can be positioned after the point in which the fluid has been introduced into twin, screw extruder 10. In one embodiment, an extraction port is positioned in close proximity to an injection port in order to; extract the fluid vapor before any additional amount of fluid is added to extruder 10. Having an extraction port in close proximity to the injection port can be useful because it may allow the user to remove the fluid before the fluid has an opportunity to react with or otherwise adversely interact with the polymer being purified. Referring to FIG. 1, extraction port 46 is integrated with sixth barrel 32F and extraction port 48 is integrated with seventh barrel 32G. In one embodiment, extraction ports 46 and 48 are in communication with a vacuum 50.

Chamber 12 can be configured so that the volume of chamber 12 incrementally increases along the length of chamber 12 so that the volume of chamber 12 matches the increase of material added to chamber 12 (e.g., the fluid). In other words, chamber 12 can be configured so that the volume of chamber 12 is in proportion to the volume of material introduced at each port so as to maintain a substantially constant mixing volume fill factor within chamber 12. Fill factors can vary in the range of 10-90% of the effective i.e., open) volume of chamber 12, and more narrowly 10-30%, to accommodate specific requirements of temperature, viscosity, dispersion and production throughput. If extraction ports 46 and 48 are sufficiently close to first and second injection ports 38 and 40, then it may not be necessary to increase the volume of chamber 12 along the length of chamber 12 because most of the fluid introduced into chamber 12 will be removed before approaching a critical fill factor.

Twin screw extruder 10 can have a die head 52 that is used to collect the purified polymer. Die head 52 can be pressurized and can eject the purified polymer through a die plate as strands into a bath 54 for cooling the purified polymer strands. The bath should contain a cooled liquid (e.g., circulating cool water) that does not adversely interact with the polymer, or add impurities to the same. Once cooled, the purified polymer is post processed by an air knife 56 and a strand pelletizer 58 for cutting the purified polymer strands into a suitable size.

Method of Forming the Coating

Herein is disclosed a method and system of purifying polymers for use with implantable medical devices, such as a stent. The implantable medical device may be any suitable medical substrate that can be implanted in a human or veterinary patient. In the interests of brevity, a drug eluting stent including a polymeric coating are described below. However, one of ordinary skill in the art will understand that other medical substrates can be manufactured using the purified polymers produced by the present invention. For example, devices that are partially or completely made from purified bioabsorbable or biostable polymers can be constructed by using the embodiments of the present invention. Such devices include stents or polymeric sheaths that are fabricated by using the purified polymer.

Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605; "MP35N," "MP20N," ELAS-TINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. As noted above, the device can also be made partially or completely from a purified bioabsorbable or biostable polymer.

After the polymer has been purified, the polymer can be applied to a stent to form a coating that is substantially biologically inert. "Purified" refers to a polymer that has had impurities removed or significantly reduced. "Impurities" refer to traces of catalysts, initiators, processing aids, suspension aids, unreacted monomers and oligomers or other low molecular weight species, or any other chemical remaining in the polymer, that can cause or effectuate an adverse biological response greater than which would occur if the impurity is removed or significantly reduced. For example, "food packaging grade" EVAL can contain impurities such as unreacted and partially reacted monomers, synthesis agents (e.g., initiators, suspension agents, etc.) and by-products such as sodium hydroxide and sodium acetate, and lower molecular weight oligomers. "Biologically inert" refers to a material that does not elicit a significantly greater adverse biological response than a biocompatible material, such as stainless steel, when implanted into a body vessel.

To fabricate the coating, the purified polymer, or a blend of purified polymers, can be applied on the stent using commonly used techniques known to those having ordinary skill in the art. For example, the polymer can be applied to the stent by dissolving the polymer in a coating solvent, or a mixture of solvents, and applying the resulting solution on the stent by spraying or immersing the stent in the solution.

Representative examples of some suitable coating solvents include chloroform, acetone, water (buffered saline), dimethylsulfoxide, propylene glycol methyl ether, iso-propylalcohol, n-propylalcohol, methanol, ethanol, tetrahydrofuran, dimethylformamide, dimethylacetamide, benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The purified polymer can also be combined with an active agent. The active agent or drug can include any substance capable of exerting a therapeutic or prophylactic effect for a patient. The drug may include small molecule drugs, peptides, proteins, oligonucleotides, and the like. The active agent could be selected, for example, to inhibit the activity of vascular smooth muscle cells. It can be directed at inhibiting abnormal or inappropriate migration and/or proliferation of smooth muscle cells to inhibit restenosis. Examples of drugs include immunosuppressive substances such as rapamycin and structural derivatives or functional analogs thereof, such as 40-O-(2-hydroxy)ethyl-rapamycin (known by the trade name of Everolimus available from Novartis), 40-O-tetrazole-rapamycin, 40-O-(3-hydroxy)propyl-rapamycin and 40-O-[2-(2-hydroxy)ethoxy]ethyl-rapamycin, and antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin antithrombin, antimitotic, antibiotic, antiallergic and antioxidant substances. Examples of such antineoplastics and/or antimitotics include paclitaxel, docetaxel, methotrexate, azathiopnrine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil ($\omega$-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon; genetically engineered epithelial cells; tacrolimus; and dexamethasone.

Coating

In an embodiment of the present invention, a stent has a coating that includes a purified polymer. The polymer can be purified by methods detailed herein. The stent can be used for implantation at a selected region of a vessel of a patient for inhibiting restenosis, and can include an active agent.

The coating for a stent including the purified polymer can have a drug-polymer layer, an optional topcoat layer, and an optional primer layer. The drug-polymer layer can be applied directly onto the stent surface to serve as a reservoir for a therapeutically active agent or drug which is incorporated into the drug-polymer layer. The topcoat layer, which can be essentially free from any therapeutic substances or drugs, serves as a rate limiting membrane for controlling the rate of release of the drug. The optional primer layer can be applied between the stent and the drug-polymer layer to improve the adhesion of the drug-polymer layer to the stent.

After purification, the polymers can be used for making either the drug-polymer layer, the topcoat membrane, the optional primer layer, or any combination thereof.

EXAMPLE

Some embodiments of the present invention are illustrated by the following Example. The Example is being given by way of illustration only and not by way of limitation. The parameters and data are not be construed to unduly limit the scope of the embodiments of the invention.

EVAL was purified using a purification system including a modified ZSK-25 mm twin screw extruder (available from Coperion Holding GmbH, Stuttgart, Germany). The system was used to perform twenty-six separate runs, each having different parameters as summarized below. The EVAL was supplied by the EVAL Company of America, Houston, Tex. Three different lots of EVAL were purified using the system: Lot 1 (manufacturer lot number LOST 31); Lot 2 (manufacturer lot number LIUB 33) and Lot 3 (manufacturer lot number LUJK 52).

The purification system used for this Example is illustrated in FIG. 1, and included a gravimetric loss-in-weight feeder for feeding the resin, two piston pumps for injecting stripping fluids, and two vent or extraction ports. The total processing barrel length was L/D=40, excluding one "dummy barrel." Each barrel was equipped with its own independent heating and cooling system.

As illustrated in FIG. 1, EVAL pellets were introduced at a feed throat at second barrel 32B of the extruder. First barrel 32A acted as a "dummy barrel." Nitrogen was bled at second barrel 32B to minimize the degradation of the melted EVAL resin. The feed throat was water-cooled. The EVAL resin was then heated in third barrel 32C, and melted and homogenized in fourth and fifth barrels 32D and 32E.

The fluids were injected into sixth and seventh barrels 32F and 32G with calibrated piston pumps. Four different fluids were used in separate runs: water, a mixture of isopropyl alcohol and water (65/35 by w/w), ethanol and DMSO. The ratio of fluid to resin was about 0.14-0.37 lbs. of fluid for ever pound of EVAL resin.

A vacuum pump was connected to sixth and seventh barrels 32F and 32G. The purified polymer was pressurized in eighth barrel 32H and discharged through a die plate of die head 52 at a 45 degree angle to bath 54 having circulating cooled water. The strand was water cooled, air knifed and pelletized.

The screw configuration for the Example is illustrated in FIG. 3. The extruder's screw con figuration was designed to provide sufficient shear rate and stress to melt the EVAL pellets. The following Table 2 provides a summary of the screw configuration. The "Element" column refers to segments of first screw 18 as illustrated in FIG. 3. Elements 13 and 20 correspond to the segments in which the fluid was injected into the extruded, whereas elements 17 and 25 correspond to the segments in which the fluid was extracted from the extruder.

The "Pitch" column refers to the ratio of width/length of first screw 18 expressed in millimeters. The width is the distance between the threads of first screw 18 and the length is the length of the corresponding, segment.

TABLE 2

| ELEMENT | PITCH (mm) | DIRECTION OF ROTATION |
|---|---|---|
| 1 | 16/16 | Right-Handed |
| 2 | 24/24 | Right-Handed |
| 3 | 36/36 | Right-Handed |
| 4 | 36/18 | Right-Handed |
| 5 | 36/36 | Right-Handed |
| 6 | 24/24 | Right-Handed |
| 7 | Not Applicable (Kneading Block) | Not Applicable (Kneading Block) |
| 8 | 24/12 | Left-Handed |
| 9 | 24/24 | Right-Handed |
| 10 | 24/12 | Right-Handed |
| 11 | 24/24 | Right-Handed |

TABLE 2-continued

| ELEMENT | PITCH (mm) | DIRECTION OF ROTATION |
|---|---|---|
| 12 | 24/12 | Right-Handed |
| 13 | 8/16 | Right-Handed |
| 14 | 16/16 | Right-Handed |
| 15 | 24/12 | Right-Handed |
| 16 | 36/36 | Right-Handed |
| 17 | 48/24 | Right-Handed |
| 18 | 36/18 | Right-Handed |
| 19 | 24/12 | Right-Handed |
| 20 | 8/16 | Right-Handed |
| 21 | 24/12 | Left-Handed |
| 22 | 16/16 | Right-Handed |
| 23 | 24/12 | Right-Handed |
| 24 | 36/36 | Right-Handed |
| 25 | 48/24 | Right-Handed |
| 26 | 36/18 | Right-Handed |
| 27 | 24/24 | Right-Handed |

As noted above, the system was used to perform twenty-six separate runs. The run conditions are summarized in the following Table 3:

TABLE 3

Run Conditions

| | Sample # | | | | | | | | |
|---|---|---|---|---|---|---|---|---|---|
| | 1 | 2 | 3 | 4 | 5 | 6 | 7 | 8 | 9 |
| Rotations/Minute Of Screws | 80 | 80 | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 | 7.5 | 7.5 |
| Torque Of Screws | 80 | 83 | 86 | 86 | 86 | 86 | 80 | 82 | 82 |
| Work On Material (kW) | 1.13 | 1.17 | 1.18 | 1.21 | 1.21 | 1.21 | 1.13 | 1.15 | 1.15 |
| EVAL Resin lot ID | 1 | 1 | 2 | 2 | 3 | 3 | 3 | 3 | 2 |
| Fluid | $H_2O$ | $H_2O$ | $H_2O$ | $H_2O$ | $H_2O$ | $H_2O$ | IPA/$H_2O$ | IPA/$H_2O$ | IPA/$H_2O$ |
| Injection Rate of Fluid (Barrel 32F) (ml/hr) | 0 | 675 | 0 | 580 | 0 | 570 | 0 | 520 | 0 |
| Injection Rate of Fluid (Barrel 32G) (ml/hr) | 525 | 525 | 500 | 500 | 490 | 490 | 540 | 540 | 560 |
| Number of Injections During Process | 1 | 2 | 1 | 2 | 1 | 2 | 1 | 2 | 1 |
| Vacuum Pressure (Barrel 32F) (mm Hg) | 2.0 | 4.5 | 1.5 | 5.8 | 2.5 | 7.0 | 2.4 | 6.2 | N/A |
| Vacuum Pressure (Barrel 32G) (mm Hg) | 6.5 | 5.5 | 4.5 | 6.3 | 5.8 | 7.2 | 4.4 | 6.2 | 7.2 |
| Temperature of Barrel 32C (° C.) | 190 | 190 | 190 | 190 | 190 | 190 | 190 | 190 | 190 |
| Temperature of Barrel 32D (° C.) | 190 | 190 | 190 | 190 | 190 | 190 | 190 | 190 | 190 |
| Temperature of Barrel 32E (° C.) | 180 | 180 | 180 | 180 | 180 | 180 | 180 | 182 | 178 |
| Temperature of Barrel 32F (° C) | 170 | 170 | 170 | 170 | 170 | 170 | 170 | 172 | 172 |
| Temperature of Barrel 32G (° C.) | 170 | 170 | 170 | 170 | 170 | 170 | 170 | 170 | 168 |
| Temperature of Barrel 32H (° C.) | 170 | 170 | 170 | 170 | 170 | 170 | 170 | 170 | 164 |

TABLE 3-continued

| Run Conditions | | | | | | | | | |
|---|---|---|---|---|---|---|---|---|---|
| Temperature of Die Head (° C.) | 190 | 190 | 190 | 190 | 190 | 190 | 190 | 190 | 190 |
| Pressure of Chamber At Discharge (lb/in$^2$) | 186 | 225 | 209 | 240 | 190 | 220 | 235 | 231 | 202 |

| | Sample # | | | | | | | |
|---|---|---|---|---|---|---|---|---|
| | 10 | 11 | 12 | 13 | 14 | 15 | 16 | 17 | 18 |
| Rotations/ Minute Of Screws | 80 | 80 | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 | 7.5 | 7.5 |
| Torque Of Screws | 87 | 82 | 80 | 78 | 80 | 78 | 7 | N/A | 79 |
| Work On Material (kW) | 1.22 | 1.15 | 1.13 | 1.10 | 1.13 | 1.10 | 1.11 | N/A | 1.11 |
| EVAL Resin lot ID | 2 | 1 | 1 | 1 | 1 | 2 | 2 | 3 | 3 |
| Fluid | IPA/H$_2$O | IPA/H$_2$O | IPA/H$_2$O | ETOH | ETOH | ETOH | ETOH | ETOH | ETOH |
| Injection Rate of Fluid (Barrel 32F) (ml/hr) | 520 | 0 | 540 | 0 | 550 | 0 | 550 | 558 | 650 |
| Injection Rate of Fluid (Barrel 32G) (ml/hr) | 500 | 540 | 540 | 640 | 648 | 650 | 650 | 558 | 550 |
| Number of Injections During Process | 2 | 1 | 2 | 1 | 2 | 1 | 2 | 1 | 2 |
| Vacuum Pressure (Barrel 32F) (mm Hg) | 7.2 | 4.0 | 6.0 | 6.0 | 7.5 | 7.0 | 8.5 | 7.0 | 7.0 |
| Vacuum Pressure (Barrel 32G) (mm Hg) | 7.2 | 5.0 | 6.0 | 6.5 | 7.0 | N/A | 9.0 | 7.5 | 7.5 |
| Temperature of Barrel 32C (° C.) | 190 | 190 | 190 | 196 | 190 | 191 | 190 | 190 | 190 |
| Temperature of Barrel 32D (° C.) | 190 | 190 | 190 | 193 | 192 | 190 | 190 | 190 | 190 |
| Temperature of Barrel 32E (° C.) | 179 | 180 | 181 | 182 | 182 | 177 | 177 | 180 | 180 |
| Temperature of Barrel 32F (° C) | 176 | 170 | 173 | 170 | 170 | 170 | 170 | 170 | 170 |
| Temperature of Barrel 32G (° C.) | 170 | 170 | 169 | 170 | 170 | 170 | 170 | 170 | 170 |
| Temperature of Barrel 32H (° C.) | 170 | 170 | 169 | 170 | 170 | 170 | 170 | 170 | 170 |
| Temperature of Die Head (° C.) | 190 | 190 | 190 | 190 | 190 | 190 | 190 | 190 | 190 |
| Pressure of Chamber At Discharge (lb/in$^2$) | 210 | 215 | 198 | 202 | 215 | 207 | 217 | 197 | 216 |

| | Sample # | | | | | | | |
|---|---|---|---|---|---|---|---|---|
| | 19 | 20 | 21 | 22 | 23 | 24 | 25 | 26 |
| Rotations/ Minute Of Screws | 80 | 80 | 80 | 80 | 80 | 80 | 80 | 80 |
| Input Rate Of Polymer (lb/hr) | 7.5 | 7.5 | 7.5 | 7.5 | 7.5 | 7.5 | 7.5 | 7.5 |
| Torque Of Screws | 76 | 68 | 75 | 66 | 75 | 67 | 72 | 66 |
| Work On Material (kW) | 1.07 | 0.96 | 1.06 | 0.93 | 1.06 | 0.94 | 1.01 | 0.93 |
| EVAL Resin lot ID | 3 | 3 | 2 | 2 | 1 | 1 | 1 | 1 |
| Fluid | DMSO | DMSO | DMSO | DMSO | DMSO | DMSO | DMSO | DMSO |
| Injection Rate of Fluid (Barrel 32F) (ml/hr) | 0 | 680 | 0 | 680 | 0 | 580 | 0 | 0 |

TABLE 3-continued

| | | | | Run Conditions | | | | |
|---|---|---|---|---|---|---|---|---|
| Injection Rate of Fluid (Barrel 32G) (ml/hr) | 540 | 540 | 550 | 550 | 550 | 550 | 283 | 540 |
| Number of Injections During Process | 1 | 2 | 1 | 2 | 1 | 2 | 1 | 1 |
| Vacuum Pressure (Barrel 32F) (mm Hg) | 6.0 | 7.0 | 6.0 | 8.5 | N/A | 8.0 | Ambient | Ambient |
| Vacuum Pressure (Barrel 32G) (mm Hg) | 4.5 | 6.5 | 7.5 | 9.0 | N/A | 8.5 | Ambient | Ambient |
| Temperature of Barrel 32C (° C.) | 190 | 190 | 190 | 190 | 190 | 190 | 190 | 190 |
| Temperature of Barrel 32D (° C.) | 190 | 190 | 190 | 190 | 190 | 190 | 190 | 190 |
| Temperature of Barrel 32E (° C.) | 180 | 180 | 180 | 180 | 180 | 180 | 180 | 180 |
| Temperature of Barrel 32F (° C) | 169 | 172 | 171 | 171 | 171 | 171 | 171 | 171 |
| Temperature of Barrel 32G (° C.) | 170 | 170 | 170 | 170 | 170 | 170 | 170 | 170 |
| Temperature of Barrel 32H (° C.) | 169 | 170 | 170 | 170 | 170 | 170 | 170 | 170 |
| Temperature of Die Head (° C.) | 190 | 190 | 190 | 190 | 190 | 190 | 190 | 190 |
| Pressure of Chamber At Discharge (lb/in$^2$) | 210 | 215 | 207 | 147 | 157 | 134 | 120 | 75 |

It was observed that the visual appearance of the purified EVAL was significantly improved. In particular, much of the discoloration of the EVAL resin was removed by the process. Additionally, the purified EVAL resin was produced in less than four hours, significantly faster than other methods of purification.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing an implantable medical device, comprising:
   purifying a polymer by:
   introducing the polymer into an extruder;
   introducing a fluid into the extruder;
   mixing the fluid with the polymer;
   removing at least a volume of the fluid from the extruder such that an impurity is completely or at least partially removed with the fluid; and
   collecting the polymer after removal of the impurity; and
   coating an implantable medical device with the purified polymer, or fabricating the implantable medical device with the purified polymer;
   wherein the fluid is of a type to physically entrap the impurity without dissolving the impurity or the fluid is of a type to dissolve the impurity.

2. The method of claim 1, wherein the extruder is selected from the group consisting of a single screw extruder, an intermeshing co-rotating extruder and a counter-rotating twin-screw extruder.

3. The method of claim 1, wherein the polymer is exposed to a temperature equal to or greater than the melting temperature of the polymer.

4. The method of claim 1, further comprising heating the polymer to a temperature equal to or greater than the melting temperature of the polymer.

5. The method of claim 1, the method further comprising introducing a second fluid into the extruder, and mixing the second fluid with the polymer and removing the second fluid and an impurity from the extruder.

6. The method of claim 1, wherein the polymer is selected from the group consisting of an ethylene vinyl alcohol copolymer, poly(butyl methacrylate), poly(vinylidene fluoride-co-hexafluororpropene), polyvinylidene fluoride, poly (L-lactic acid), poly(caprolactone), an ethylene-vinyl acetate copolymer and polyethylene glycol.

7. The method of claim 1, wherein the fluid is selected from the group consisting of water, isopropyl alcohol, methanol, FLUX REMOVER AMS, acetone, ethanol, dimethyl acetamide, acetonitrile, dimethyl formamide, cyclohexane, dimethyl sulfoxide, and combinations thereof.

8. The method of claim 1, further comprising exposing the fluid to a temperature equal to or greater than the boiling temperature of the fluid at ambient pressure prior to removing the fluid from the extruder.

9. A method of manufacturing a coating for an implantable medical device, comprising:
   (a) purifying a thermoplastic polymer, the purifying including introducing the polymer into an extruder,
   introducing a fluid into the extruder,
   mixing the fluid with the polymer,
   removing at least a portion of the fluid and an impurity from the extruder, and collecting the polymer after removal of the impurity; and (b) applying a composition to an implantable medical device, the composition including the purified polymer, a solvent and optionally a therapeutic agent;

wherein the fluid is of a type to physically entrap the impurity without dissolving the impurity or the fluid is of a type to dissolve the impurity.

10. The method of claim 9, the method further comprising exposing the polymer to a temperature equal to or greater than the melting temperature of the polymer while the polymer is in the extruder.

11. The method of claim 9, wherein the polymer is selected from the group consisting of an ethylene vinyl alcohol copolymer, poly(butyl methacrylate), poly(vinylidene fluoride-co-hexafluororpropene), polyvinylidene fluoride, poly (L-lactic acid), poly(caprolactone), an ethylene-vinyl acetate copolymer and polyethylene glycol.

12. The method of claim 9, wherein the fluid is selected from the group consisting of water, isopropyl alcohol, methanol, FLUX REMOVER AMS, acetone, ethanol, dimethyl acetamide, acetonitrile, dimethyl formamide, cyclohexane, dimethyl sulfoxide, and combinations thereof.

13. The method of claim 9, wherein the purifying further includes introducing a second fluid into the extruder, and mixing the second fluid with the polymer and removing the second fluid and the impurity from the extruder, wherein the second fluid is of a type that dissolves the impurity and the second fluid is not the same as the first fluid.

14. The method of claim 9, further comprising exposing the fluid to a temperature equal to or greater than the boiling temperature of the fluid at ambient pressure prior to removing the fluid.

15. A method of manufacturing an implantable medical device, comprising:

purifying a polymer by:

introducing the polymer into an extruder;

introducing a fluid into the extruder, the fluid selected from the group consisting of FLUX REMOVER AMS, dimethyl acetamide, dimethyl formamide, dimethyl sulfoxide, and combinations thereof;

mixing the fluid with the polymer;

removing at least a volume of the fluid from the extruder such that an impurity is completely or at least partially removed with the fluid; and collecting the polymer after removal of the impurity; and coating an implantable medical device with the purified polymer.

16. The method of claim 15, further comprising exposing the fluid to a temperature equal to or greater than the boiling temperature of the fluid at ambient pressure after the fluid has removed the impurity.

17. The method of claim 15, wherein the extruder is selected from the group consisting of a single screw extruder, an intermeshing co-rotating extruder and a counter-rotating twin-screw extruder.

18. The method of claim 15, wherein the polymer is exposed to a temperature equal to or greater than the melting temperature of the polymer.

19. The method of claim 15, further comprising heating the polymer to a temperature equal to or greater than the melting temperature of the polymer.

20. The method of claim 15, wherein the fluid is of a type to physically entrap the impurity without dissolving the impurity.

21. The method of claim 15, the method further comprising introducing a second fluid into the extruder, and mixing the second fluid with the polymer and removing the second fluid and an impurity from the extruder.

22. A method of manufacturing an implantable medical device, comprising:

purifying a polymer by:

introducing the polymer into an extruder, the polymer having an impurity;

introducing a first fluid into the extruder, the first fluid acting as a solvent for the impurity;

mixing the first fluid with the polymer;

removing at least a volume of the first fluid from the extruder such that the impurity is at least partially removed with the first fluid;

introducing a second fluid into the extruder, the second fluid acting as a non-solvent for the impurity;

mixing the second fluid with the polymer;

removing at least a volume of the second fluid from the extruder such that the impurity is at least partially removed with the second fluid; and collecting the polymer after removal of the impurity; and coating an implantable medical device with the collected polymer, or fabricating the implantable medical device with the collected polymer, wherein the second fluid is not the same as the first fluid.

23. The method of claim 22, wherein after the first fluid has removed the impurity, exposing the first fluid to a temperature equal to or greater than the boiling temperature of the first fluid at ambient pressure prior to removing the first fluid from the extruder.

24. The method of claim 22, wherein after the second fluid has removed the impurity, exposing the second fluid to a temperature equal to or greater than the boiling temperature of the second fluid at ambient pressure prior to removing the second fluid from the extruder.

25. The method of claim 22, wherein the polymer is poly (vinylidene fluoride-co-hexafluororpropene) or poly(butyl methacrylate).

* * * * *

UNITED STATES PATENT AND TRADEMARK OFFICE
CERTIFICATE OF CORRECTION

PATENT NO. : 7,645,474 B1
APPLICATION NO. : 10/631228
DATED : January 12, 2010
INVENTOR(S) : Pathak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this

Twenty-eighth Day of December, 2010

David J. Kappos
*Director of the United States Patent and Trademark Office*